(12) United States Patent
Gregory, II

(10) Patent No.: US 12,129,064 B2
(45) Date of Patent: Oct. 29, 2024

(54) HANGER APPARATUS

(71) Applicant: Product Launch Advisors, LLC, York, SC (US)

(72) Inventor: Richard O. Gregory, II, Rock Hill, SC (US)

(73) Assignee: Product Launch Advisors, LLC, York, SC (US)

( * ) Notice: Subject to any disclaimer, the term of this patent is extended or adjusted under 35 U.S.C. 154(b) by 474 days.

(21) Appl. No.: 17/335,961

(22) Filed: Jun. 1, 2021

(65) Prior Publication Data

US 2021/0371206 A1 Dec. 2, 2021

Related U.S. Application Data

(60) Provisional application No. 63/033,368, filed on Jun. 2, 2020.

(51) Int. Cl.
| | |
|---|---|
| *B65B 55/02* | (2006.01) |
| *A61L 2/10* | (2006.01) |
| *A61L 2/26* | (2006.01) |
| *A61L 2/28* | (2006.01) |
| *B65D 5/42* | (2006.01) |
| *B65D 25/22* | (2006.01) |
| *B65D 75/56* | (2006.01) |
| *B65G 17/20* | (2006.01) |
| *B65G 17/36* | (2006.01) |
| *G01J 1/42* | (2006.01) |
| *G01J 1/50* | (2006.01) |

(52) U.S. Cl.
CPC .............. *B65B 55/02* (2013.01); *A61L 2/10* (2013.01); *B65D 5/4208* (2013.01); *B65D 25/22* (2013.01); *B65D 75/56* (2013.01); *B65G 17/20* (2013.01); *B65G 17/36* (2013.01); *G01J 1/429* (2013.01); *G01J 1/50* (2013.01); *A61L 2/28* (2013.01); *A61L 2202/122* (2013.01); *B65D 2575/565* (2013.01); *B65G 2207/26* (2013.01)

(58) Field of Classification Search
None
See application file for complete search history.

(56) References Cited

U.S. PATENT DOCUMENTS

| | | | | |
|---|---|---|---|---|
| 2003/0170399 | A1* | 9/2003 | Owed, Jr. | ............... B05B 5/082 |
| | | | | 118/500 |
| 2011/0155915 | A1* | 6/2011 | Brueck | ................... B65B 55/02 |
| | | | | 250/455.11 |
| 2015/0262516 | A1* | 9/2015 | White | ..................... A47F 13/06 |
| | | | | 40/606.03 |
| 2019/0070325 | A1* | 3/2019 | Preminger | ................ A61L 2/10 |

(Continued)

OTHER PUBLICATIONS

Advanced UV Systems; Article entitled: "The UV Cube", located at <https://www.advanceduvsystems.com/uv-cube, accessed on May 28, 2021, 2 pgs.

(Continued)

*Primary Examiner* — Eliza W Osenbaugh-Stewart
(74) *Attorney, Agent, or Firm* — Taylor English Duma LLP

(57) ABSTRACT

A hanger can include an elongated body defining: a first end defining at least one aperture; and a second end, the first end and the second end defined at opposite ends of the hanger along a longitudinal direction, the hanger being configured to support a hanging object at the second end; and a UV indicator.

20 Claims, 10 Drawing Sheets

(56) References Cited

U.S. PATENT DOCUMENTS

2020/0360549 A1* 11/2020 Neveu .................... A61B 50/20

OTHER PUBLICATIONS

Advanced UV Systems; Article entitled: "KR615 Germicidal Enclosure: The UV Box", located at <https//www.advanceduvsystems.com/the-uv-box>, accessed on May 28, 2021, 3 pgs.

Advanced UV Systems; Article entitled: "Ray UV-C", available at <https://www.advanceduvsystems.com/ray-uv-c>, accessed on May 28, 2021, 2 pgs.

Advanced UV Systems; User's Manual for KR615 Germicidal Enclosure, available prior to Jun. 1, 2021, 17 pgs.

UV Process Supply, Inc.; Article entitled: "New UV Intensity Labels", located at <https://www.uvprocess.com/uv-intensity-labels/1969-new-uv-intensity-labels.html#1548-part_no-n010-005>, accessed on May 20, 2021, 5 pgs.

UV Process Supply, Inc.; Instructions for New UV Intensity Labels, Copyright 2005, 2 pgs.

* cited by examiner

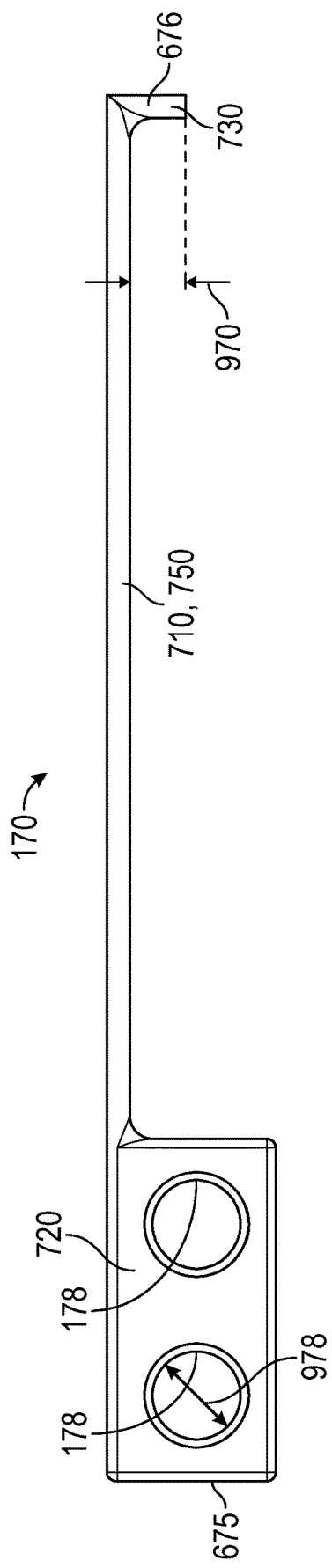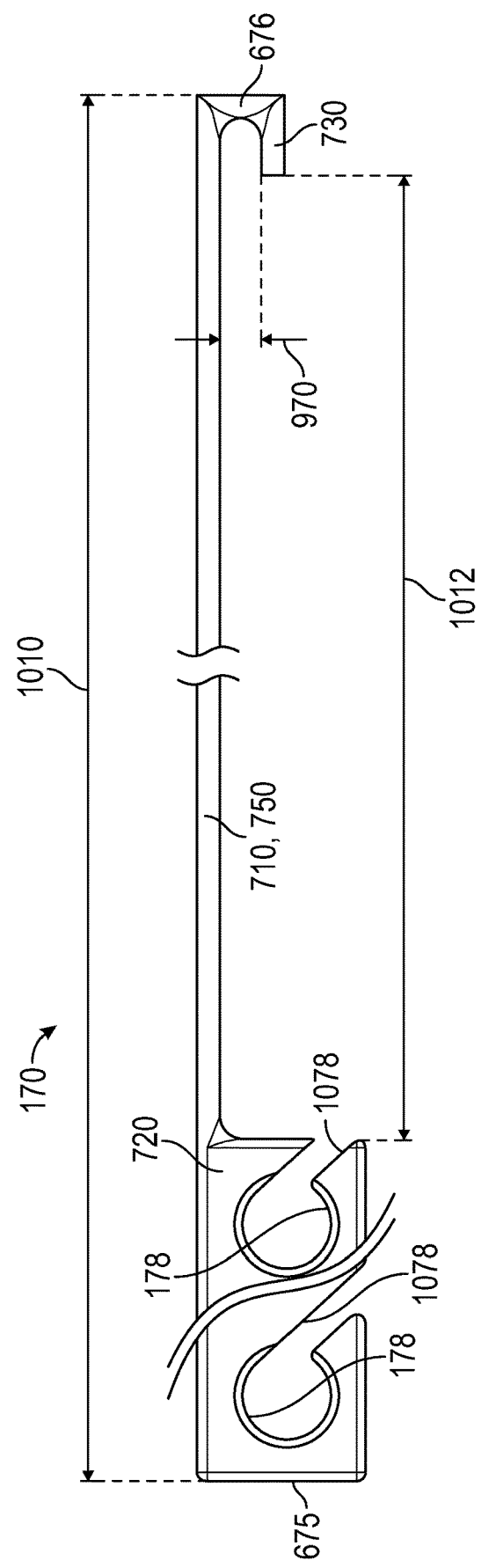

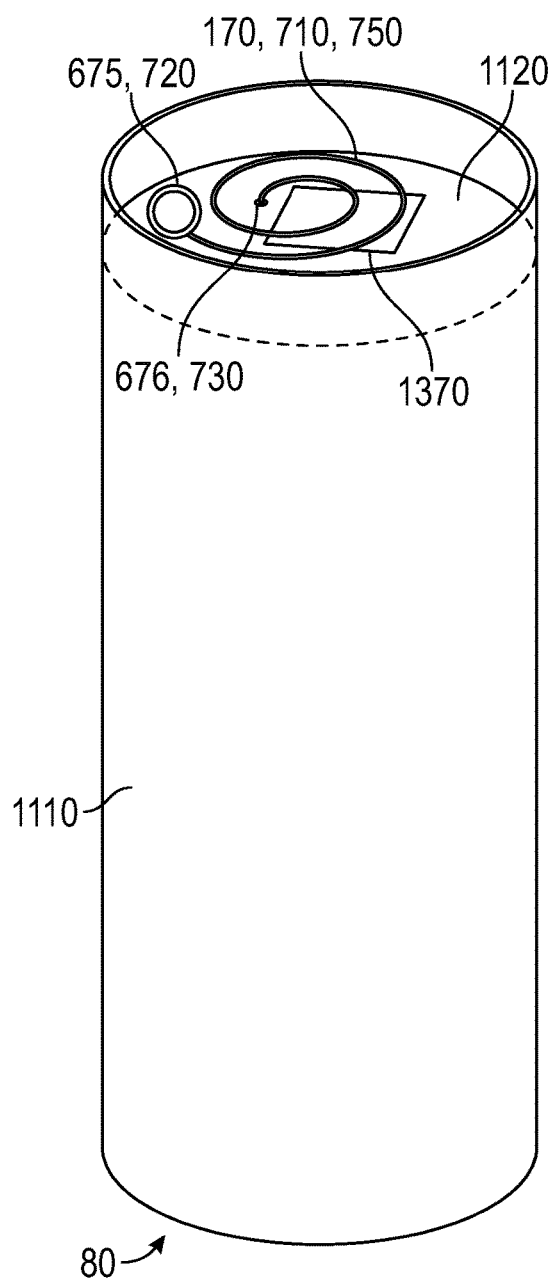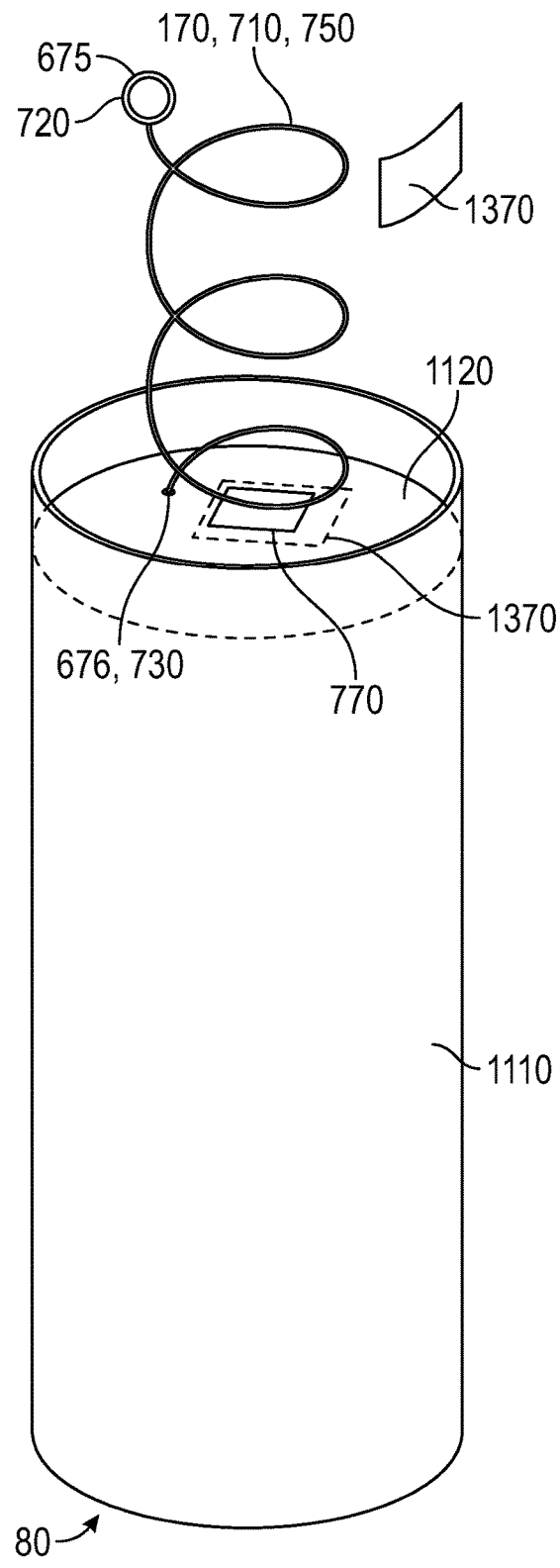
FIG. 13                    FIG. 14

HANGER APPARATUS

REFERENCE TO RELATED APPLICATIONS

This application claims the benefit of U.S. Provisional Application No. 63/033,368, filed Jun. 2, 2020, which is hereby specifically incorporated by reference herein in its entirety.

TECHNICAL FIELD

Field of Use

This disclosure relates to systems for sterilizing objects with UV light. More specifically, this disclosure relates to sterilizing objects with UV light by suspending the objects with hangers in the vicinity of the UV light such that the UV light is not blocked.

Related Art

In a world in which invisible bacteria and viruses can have widespread impact, it can be beneficial to sterilize or sanitize even everyday objects such as, for example and without limitation, packages that are sent and received daily in increasing quantities. Systems for suspending and/or sterilizing objects including but not limited to packages are not widely available, if at all. Where systems exist for sterilizing other objects (e.g., small to medium electronic devices), they can involve placing the objects on shelves formed from quartz rods, which can be fragile and expensive and impractical for use with some objects—especially when processed in high volume and in a wide range of sizes, shapes, and weights.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, disclosed is a hanger comprising: an elongated body defining: a first end defining at least one aperture; and a second end, the first end and the second end defined at opposite ends of the hanger along a longitudinal direction, the hanger being configured to support a hanging object at the second end; and a UV indicator.

In a further aspect, disclosed is a system comprising: a hanger configured to suspend an object to be sterilized; a UV generator configured to irradiate the object with UV light; and a hanger-receiving retainer configured to receive the hanger.

In yet another aspect, disclosed is a method comprising: suspending an object with a hanger; and irradiating the object with UV radiation from a UV generator.

Various implementations described in the present disclosure may comprise additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations may be realized and obtained by means of the systems, methods, features particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate several aspects of the disclosure and together with the description, serve to explain various principles of the disclosure. The drawings are not necessarily drawn to scale. Corresponding features and components throughout the figures may be designated by matching reference characters for the sake of consistency and clarity.

FIG. 9 is a front plan view of the hanger of FIG. 7.

FIG. 10 is a front plan view of the hanger of FIG. 7 in accordance with another aspect of the current disclosure.

FIG. 13 is a top perspective view of the object of FIG. 1 in accordance with another aspect of the current disclosure, the object comprising a tube and an integrated hanger in a non-extended position.

FIG. 14 is a top perspective view of the object of FIG. 13 with the integrated hanger in an extended position.

DETAILED DESCRIPTION

Figure 1:
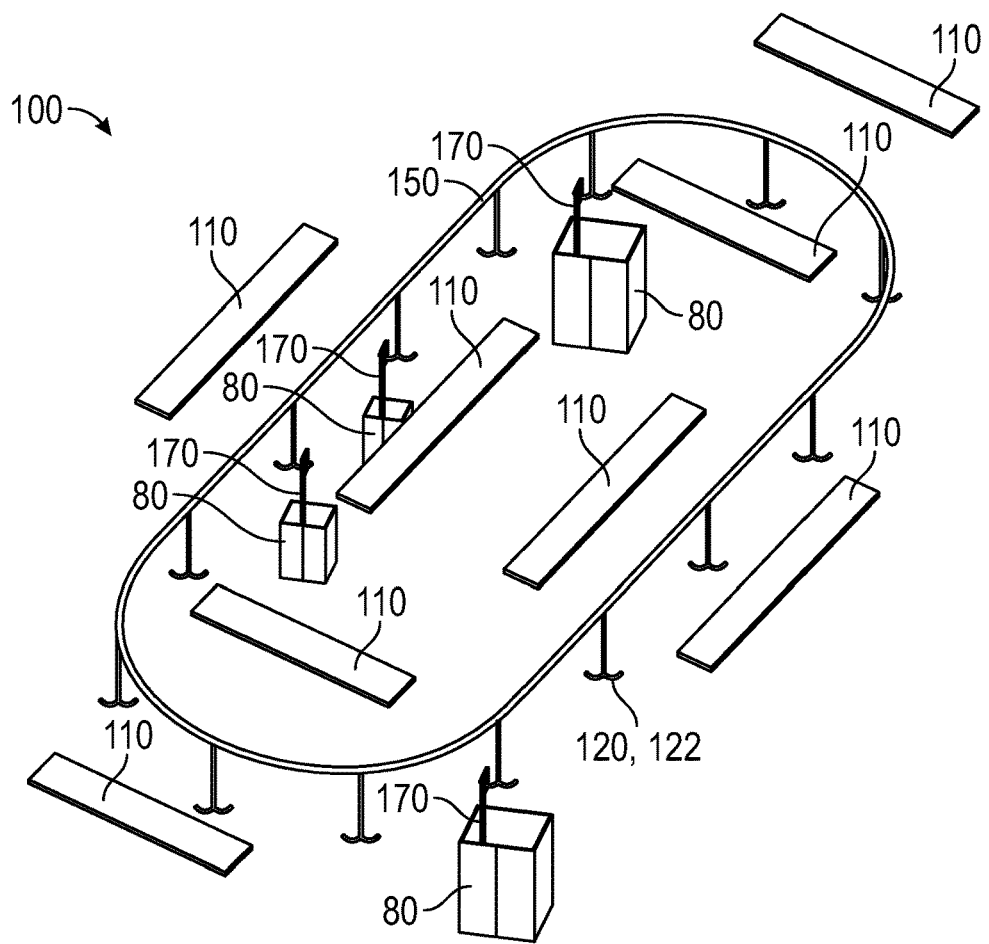
FIG. 1 is a top perspective view of a system comprising a conveyor, a plurality of objects suspended from the conveyor with a plurality of hangers, and a plurality of UV generators in accordance with one aspect of the current disclosure.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

The following description is provided as an enabling teaching of the present devices, systems, and/or methods in their best, currently known aspect. To this end, those skilled in the relevant art will recognize and appreciate that many changes can be made to the various aspects described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. Similarly, a stated range of "1 to 10" should be considered to include any and all subranges beginning with a minimum value of 1 or more and ending with a maximum value of 10 or less, e.g., 1 to 6, 3 to 9, or 4 to 7.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

As used throughout, the singular forms "a," "an" and "the" include plural referents unless the context clearly dictates otherwise. Thus, for example, reference to a quantity of one of a particular element can comprise two or more such elements unless the context indicates otherwise. In addition, any of the elements described herein can be a first such element, a second such element, and so forth (e.g., a first widget and a second widget, even if only a "widget" is referenced).

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about" or "substantially," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list. The phrase "at least one of A and B" as used herein means "only A, only B, or both A and B"; while the phrase "one of A and B" means "A or B."

In one aspect, a system for sterilizing objects with UV light and associated methods, systems, devices, and various apparatuses are disclosed herein. In one aspect, the system can comprise a hanger, which can be formed separately from or integrally with an object to be sterilized with the system.

FIG. 1 is a top perspective view of a system 100, which can be a hanger system, in accordance with one aspect of the current disclosure. The system 100 can comprise a conveyor 150. The system 100 can comprise one or more hanger-receiving retainers 120, which can be configured to receive a hanger 170. The system 100 can comprise one or more of the hangers 170, which can be configured to suspend an object 80 to be sterilized. The system 100 can comprise one or more UV generators 110. The system 100 can comprise one or more of the objects 80, which can be sterilized by the system 100. More specifically, in some aspects, a plurality of objects 80 can be suspended from the conveyor 150 with a plurality of hangers 170 and movement of the objects 80 by the conveyor 150 past the one or more UV generators, which can be configured to irradiate surfaces of the objects 80 with UV light. Each of the components of the system 100, including those disclosed herein, can be housed or positioned within an enclosure 230 (shown in FIG. 2).

The conveyor 150 can comprise a track and can be supported as desired through a support structure familiar to one of ordinary skill in the corresponding art. In some aspects, as shown, the conveyor 150 can define a closed shape. In other aspects, the conveyor 150 need not define a closed shape. For example and without limitation, the conveyor 150 can define a linear arrangement or one otherwise defining separate start and end points. Any one of a variety of conveyor designs can be used such as a beam or I-beam conveyor design or an enclosed-track conveyor design. For example and without limitation, the beam conveyor design can comprise beam track Part No. 5920K2 and trolley Part No. 5920K24; and the enclosed-track conveyor design can comprise beam track Part No. 5927K11 and trolley Part No. 5927K42, all of which is available from McMaster-Carr Supply Company of Elmhurst, Illinois. The conveyor 150 can further comprise one more each of brackets, motor drive systems comprising motors, controllers, or other components as desired by a user.

The hanger-receiving retainer 120 can immobilize, i.e., fix a position of in one or more directions, the hanger 170 with respect to the hanger-receiving retainer 120, such as by grasping or hooking one or more apertures 178 (shown in FIG. 7) defined in the hanger 170. As shown, the hanger-receiving retainer 120 can comprise a hook 122, which can be inserted into one or more of the apertures 178 of the hanger 170. More specifically, the hook 122 can define a "J" shape, an "L" shape, or a barb shape. In some aspects, as shown with the conveyor 150 configured to transport the objects 80 along a path, the hanger-receiving retainer 120 can be dynamically mounted in the enclosure 230. In other aspects, the hanger-receiving retainer 120 can be statically mounted (i.e., can generally remain stationary) in the enclosure 230. In some aspects, the hanger-receiving retainer 120 can undergo rotation and/or translation within the enclosure 230.

The UV generator 110 can comprise one or more UV lights. In some aspects, the UV generator 110 can emit UV radiation towards an approximate center of the enclosure 230. The UV generator 110 can be positioned above, below, to the side, or in any other position with respect to the objects 80. More generally, any UV generator 110 can be positioned within the enclosure 230 in any manner not inconsistent with the objectives of this disclosure. In some aspects, it will be beneficial—and possible—to expose all sides or surfaces of each object 80 to the UV light by using the hanger 170 to suspend the object 80 because the hanger 170 will permit all surfaces of the object 80 to be exposed to the UV light emitted by the UV generator 110.

In some aspects, to minimize cost, the UV generator 110 can comprise a UV fluorescent light. In some aspects, to maximize durability, the UV generator 110 can comprise a UV light comprising an LED (light-emitting diode). The UV light generated can be in the UV-A light wavelength range (320-400 nanometers or nm), the UV-B light wavelength range (290-320 nm), or the UV-C light wavelength range (100-290 nm). To maximize strength and effectiveness of the UV light, the wavelength of the UV light generated can be in the UV-C light wavelength range. The one or more UV generators 110 can be configured to produce any range of desired light intensity output such as, for example and without limitation, 250 mW/cm². In some aspects, it will be advantageous to uniformly flood all surfaces of the object 80 with the same intensity of UV light, which can reduce the amount of exposure time and/or increase the capacity of the system 100 to sanitize the objects 80.

Figure 2:
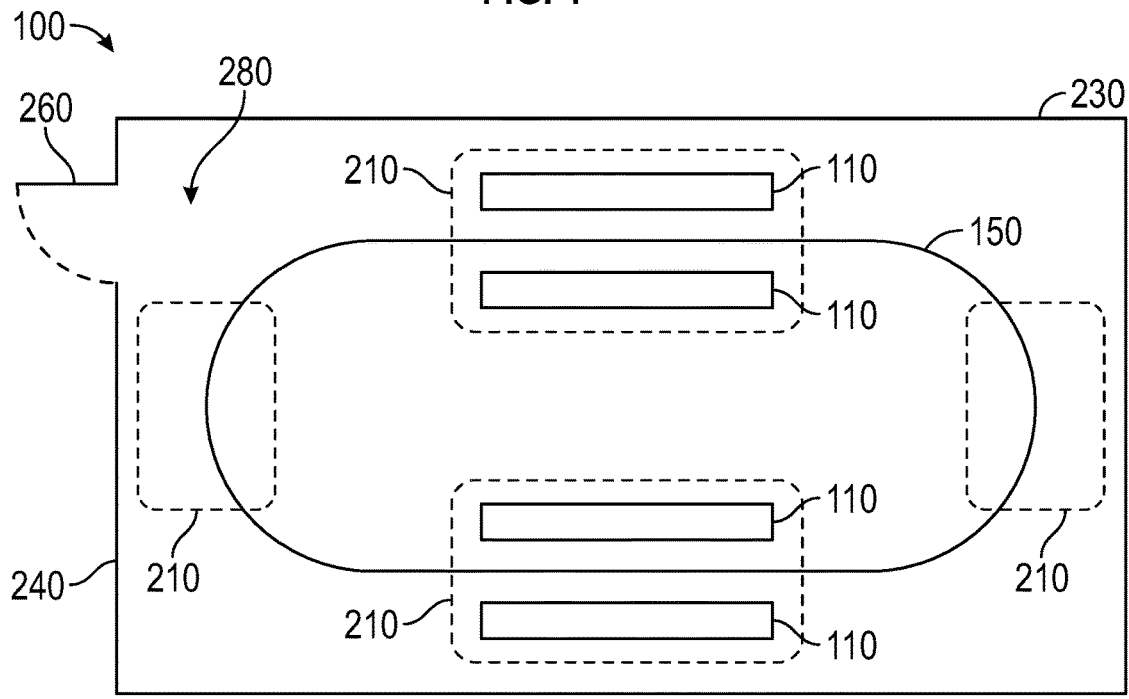
FIG. 2 is a top plan view of the system of FIG. 1, further comprising an enclosure in accordance with another aspect of the current disclosure.

FIG. 2 is a top plan view of the system 100 of FIG. 1 in accordance with another aspect of the current disclosure. As shown, the enclosure 230 can define a housing 240, which can be a room, and a door 260, which can provide access to an interior cavity or interior 280 of the housing 240 and, more generally, the enclosure 230. The system 100 can comprise one or more stations 210, any of which can comprise a UV generator 110 or can be used to load and/or remove objects 80 from the system 100.

Figure 3:
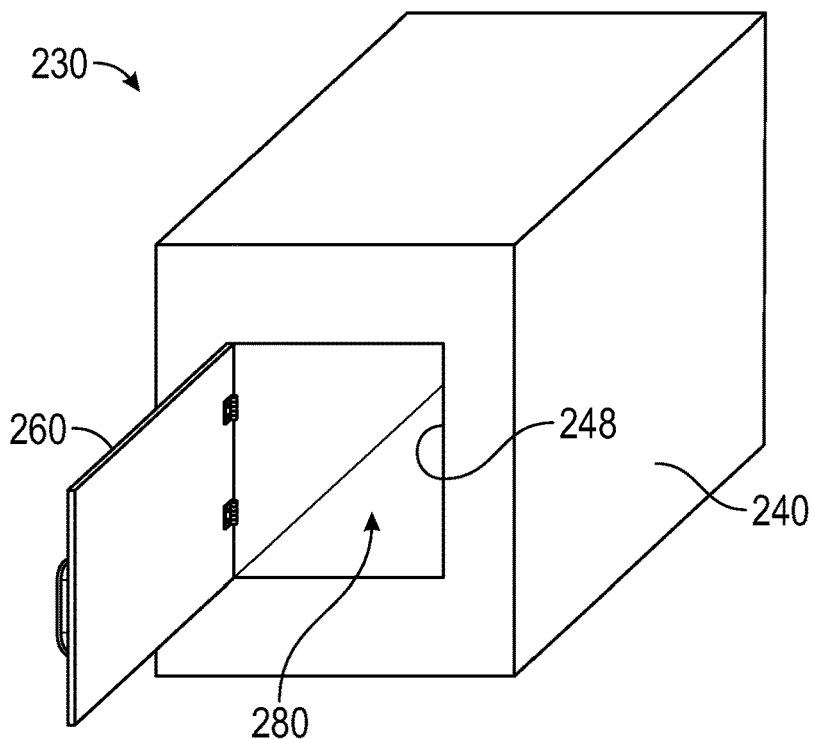
FIG. 3 is a front perspective view of an enclosure in accordance with another aspect of the current disclosure and with a door of the enclosure in an open position.

FIG. 3 is a front perspective view of the enclosure 230 comprising the housing 240 in accordance with another aspect of the current disclosure and with the door 260 of the housing 240 in an open position. The door 260 can be mounted to the housing 240—and, in some aspects, hingedly mounted, as shown—and can be configured to close an opening 248 defined in the housing 240. The enclosure 230 and the interior 280 defined thereby can be sized to receive any one or more of the objects 80 (shown in FIG. 1), which can be of any size including the sizes of packages able to be shipped and suspended by the hanger 170. The door 260 of the enclosure 230 can have an open position, as shown, and a closed position (shown in FIG. 5). The hanger-receiving retainer 120 can be statically mounted in the enclosure 230, as shown in FIG. 6, or can be dynamically mounted in the enclosure 230, i.e., mounted in such a way that the hanger-receiving retainer 120 can move inside the enclosure 230, such as shown in the conveyor type system illustrated in FIG. 1. Additionally, the hanger-receiving retainer 120 can undergo rotation and/or translation within the housing 240 during use, which can facilitate full exposure of the object 80 to UV light from the one or more UV generators 110. In some aspects, a surface of the enclosure 230 or a surface inside the enclosure 230 can comprise or define a reflective material, which can be configured to reflect UV light.

Figure 4:
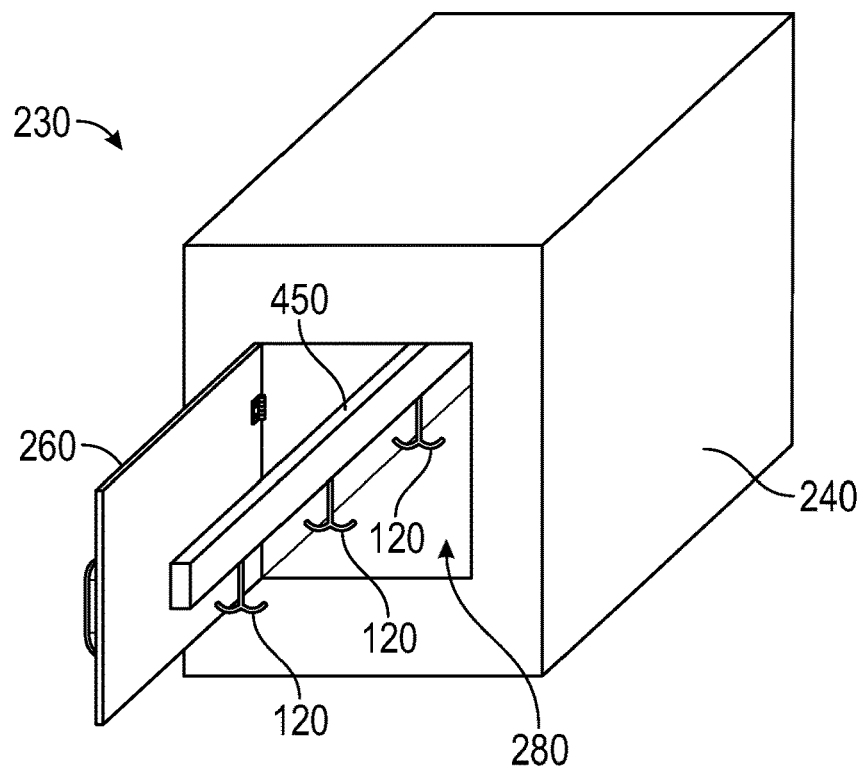
FIG. 4 is a front perspective view of the enclosure of FIG. 4 comprising a retractable support rail in accordance with another aspect of the current disclosure.

FIG. 4 is a front perspective view of the enclosure 230 of FIG. 4, which can, as shown, comprise a retractable support rail 450 in accordance with another aspect of the current disclosure. The support rail 450, which can comprise one or more hanger-receiving retainers 120, can comprise a sliding track such as that used in the conveyor 150 or that used in drawer slides and comprising rolling elements such as, for example and without limitation, wheels and/or ball bearings. As shown, the support rail 450 can extend from the opening 248 defined in the housing 240 and can thereby facilitate loading and unloading of the object 80 (shown in FIG. 1) therefrom the support rail 450. The support rail 450 can also be fully retracted into the housing 240 and the interior 280 during sterilization of the object 80 by UV light to a degree that the door 260 can be closed against the opening 248.

Figure 5:
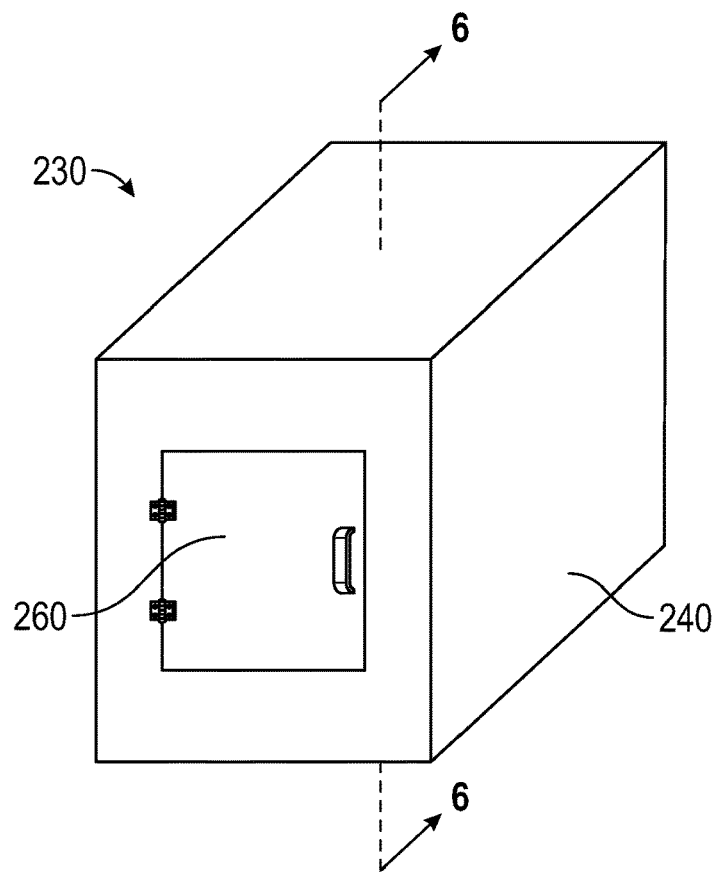
FIG. 5 is a front perspective view of the enclosure of FIGS. 3 and 4 in accordance with another aspect of the current disclosure and with the door of the housing closed.
Figure 6:
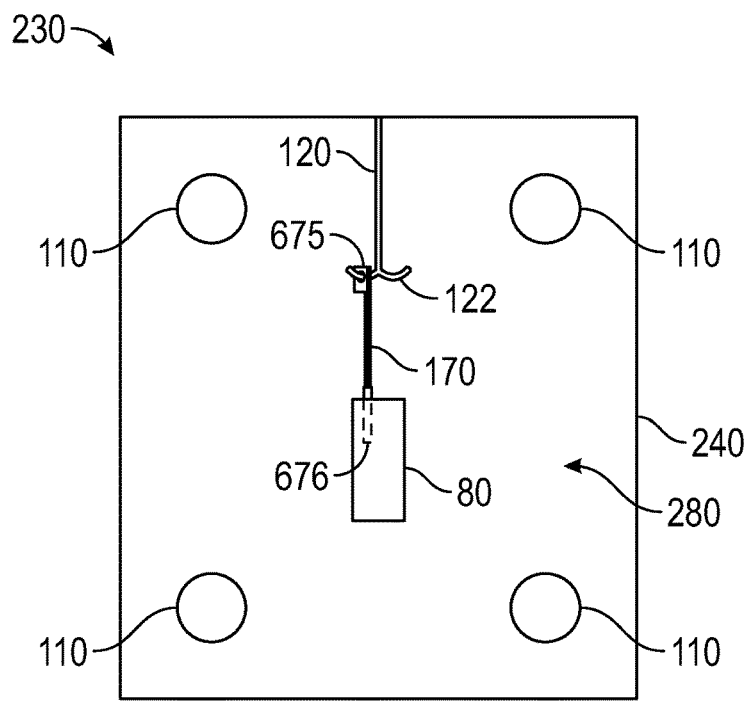
FIG. 6 is a sectional view of the enclosure of FIGS. 3 and 4 taken along line 6-6 of FIG. 5 and further comprising a plurality of UV generators and an object suspended therebetween by one of the plurality of hangers of FIG. 1.

FIG. 5 is a front perspective view of the enclosure 230 of FIG. 4 in accordance with another aspect of the current disclosure and with the door 260 of the enclosure 230 closed against the housing 240. In some aspects, when the door 260 is in a closed position, the UV generator 110 can be configured to emit UV radiation into the interior 280 (shown in FIG. 3) of the housing 240, and when the door 260 is in an open position, the UV generator 110 can be configured to not emit UV radiation. Accordingly, the UV generator 110 can be configured to emit UV radiation only when the door 260 of the enclosure 230 is closed. For example, a switch or sensor sensing a position of the door 260 can signal to a controller of the UV generator 110 that the door 260 is either open or closed, and the UV generator 110 can respond accordingly.

FIG. 6 is a sectional view of the enclosure 230 of FIG. 4 taken along line 6-6 of FIG. 5 and further comprising a plurality of UV generators 110 and one instance of the object 80 suspended by the hanger 170 therebetween and inside the interior 280. Again, the hanger-receiving retainer 120 can be suspended from and supported by the housing 240 of the enclosure 230, the hanger 170 can be suspended from and supported by the hanger-receiving retainer 120—and, more specifically, the hook 122 thereof, and the object 80 can be suspended from and supported by the hanger 170. More specifically, in some aspects, a first end 675 of the hanger 170 can be suspended from and supported by the hanger-receiving retainer 120, and the object 80 can be suspended from and supported by a second end 676 of the hanger 170. In some aspects, as described above, the hanger-receiving retainer 120 can be hook-shaped—comprising, for example, the hook 122—and can be inserted into one or more of the apertures 178 (shown in FIG. 7) of the hanger 170.

Figure 7:
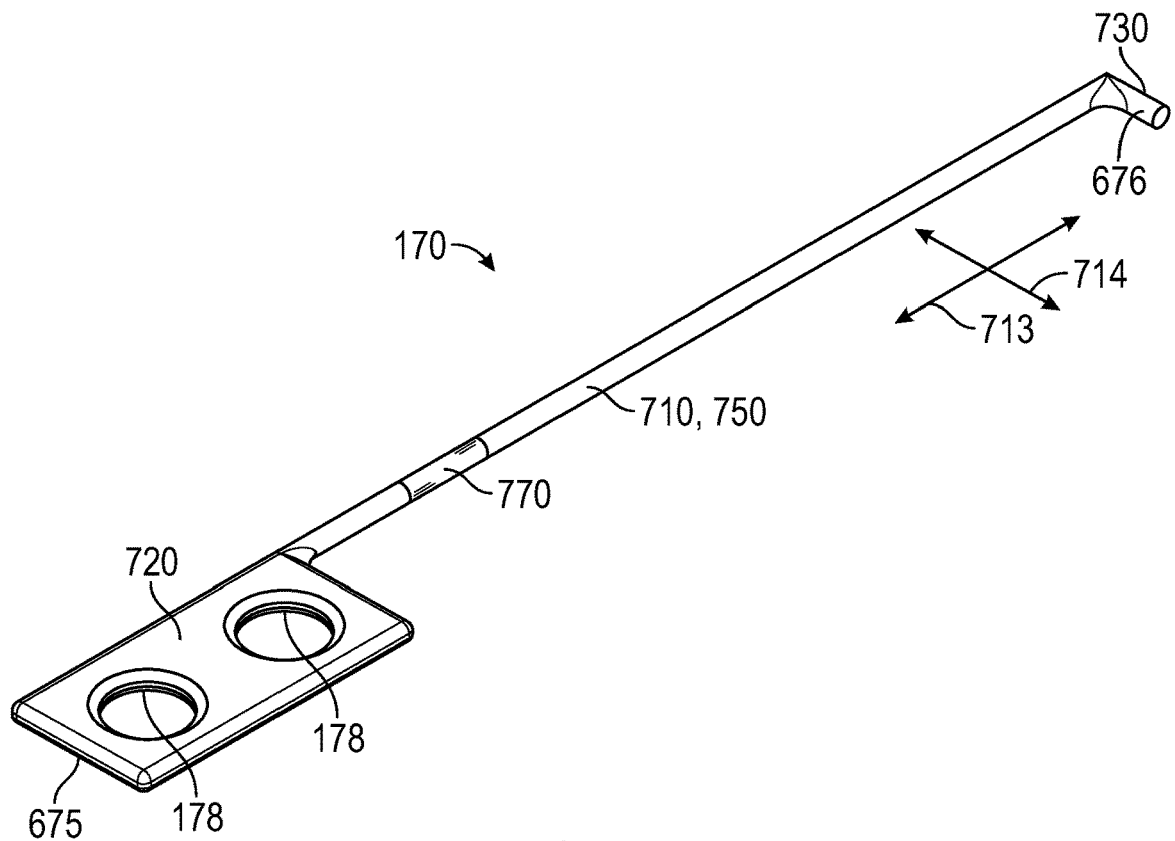
FIG. 7 is a top front perspective view of one of the plurality of hangers of FIG. 1.

FIGS. 7-10 and 12 show various aspects of a hanger that is discrete or separate from the object 80 it can be configured to support. FIG. 7 is a top perspective view of one of the plurality of hangers 170 of FIG. 1. As described above, the hanger 170 can be used to hold or suspend the object 80 (shown in FIG. 1), which can be a package or parcel, while the object is sterilized with UV light. The hanger 170 can comprise an elongated body 710 having or defining the first end 675 and having or defining the second end 676. The first end 675 and the second end 676 can be defined at opposite ends of the hanger 170 along a longitudinal axis or direction 713. The hanger 170 can be configured to support a hanging object such as the object 80 (shown in FIG. 1) at the second end 676.

The first end 675 can have or define one or more of the apertures 178 and comprise a first portion 720. The first portion 720 can define a substantially wide and flat shape such that a width 815 (shown in FIG. 8) is substantially greater than a thickness 810 (shown in FIG. 8) of the first portion. This can facilitate rotation of the hanger 170 inside an opening 1280 (shown in FIG. 12) by manual rotation by a hand of a user of the system 100. In some aspects, the width 815 can be at least 5 times greater than the thickness 810. In some aspects, the width 815 can be at least 7.5 times greater than the thickness 810. In some aspects, the width 815 can be at least 10 times greater than the thickness 810. When defined in the first end 675, a plurality of the apertures 178 can extend along or approximately along the longitudinal direction 713 of the elongated body 610, can extend in a direction angled with respect with or, more specifically, normal to the longitudinal direction 713, i.e., in a transverse direction 714, or can be arranged in rows and columns relative to the longitudinal direction 713. The plurality of apertures 178 can have the same or different inside diameters 978 (shown in FIG. 9).

Figure 8:
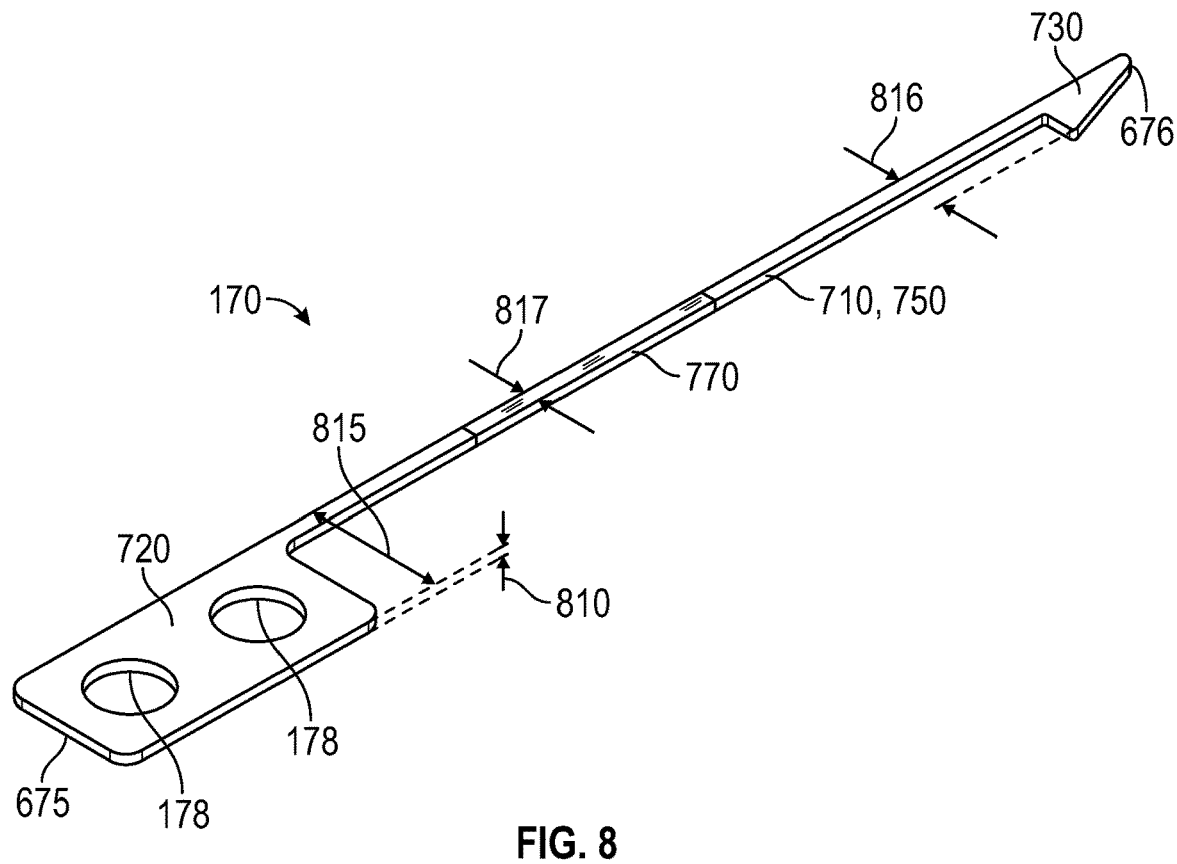
FIG. 8 is a top front perspective view of one of the plurality of hangers of FIG. 1 in accordance with another aspect of the current disclosure.

The second end 676, which can be distal from the first end 675, can comprise a hook portion or hook 730. A middle portion 750 can extend from the first end 675 to the second end 676 and between the first portion 720 and the hook 730. The hook 730 can be any shape not inconsistent with the objectives of this disclosure such as, for example and without limitation a "J" shape (as shown in FIG. 10), an "L" shape (as shown in FIG. 7), or a barb shape (as shown in FIG. 8). The hook 730 can be expandable, i.e., can vary in size and shape as desired to accommodate various objects 80.

As shown, various edges or other geometric features of the hanger 170 can define radii or chamfers to improve ergonomics, facilitate manufacturability, and/or reduce weight of the hanger 170. The elongated body 710 and, more generally, the hanger 170 can be made of any material not inconsistent with the objectives of this disclosure, including a metal, a wood, a paper, a cardboard, or a plastic. The components of the system 100, including the hanger 170, can be manufactured using any one or more of a number of different processes. In some aspects, they can be manufactured using a molding process such as injection molding. In other aspects, any of these same parts can be manufactured through an additive manufacturing process such as, for example and without limitation, three-dimensional printing or through a subtractive manufacturing process such as, for example and without limitation, stamping and machining.

In some aspects, the hanger can comprise a UV exposure indicator or UV indicator 770 to provide visual confirmation that the object 80 has been exposed to UV light. In some aspects, the UV indicator 770 can be integrated into a material of the hanger 170. In some aspects, the UV indicator 770 can comprise an externally adhered sticker (comprising paper, for example and without limitation, such as the New UV Intensity Labels product available from UV Process Supply, Inc. of Chicago, Illinois, U.S.A.) or paint affixed, printed, or otherwise applied to an outer surface 711 of the elongated body 710 of the hanger 170. In some aspects, the UV indicator 770 can be integrated into the object 80 itself. The UV indicator can be a paint or ink. The UV indicator 770 can be any size and shape. In some aspects, the UV indicator 770 can be shaped to be more easily visible from a distance. The UV indicator 770 can be a strip.

The UV indicator 770 can change appearance upon exposure to UV light such as that produced by the UV generator 110 (shown in FIG. 1). More specifically, the UV indicator 770 can change appearance upon direct, physical exposure to UV light. The change in appearance can be a change in color. In some aspects, the change in appearance can be irreversible.

The UV indicator 770 can change color depending on the exposure time. As long as the exposure time is sufficient to meet or exceed a minimal dosage (sufficient to sterilize the surfaces of the object 80, for example), the UV indicator 770 can show this in the color change. A radiometer—such as a POWER PUCK II UV Radiometer available from EIT LLC of Leesburg, Virginia, U.S.A.—can be used with something like an Ophir meter to measure the UV light power density for a given exposure time and distance.

FIG. 8 is a top perspective view of one of the plurality of hangers 170 of FIG. 1 in accordance with another aspect of the current disclosure. As shown, a diameter or width 817 of a portion of the elongated body 710 between the first end 675 and the second end 676 such as the middle portion 750 can be narrower than each of the width 815 of the elongated body 710 at the first end 675 and a width 816 of the elongated body 710 at the second end 676. As shown, the thickness 810 of the hanger 170 can be constant and, as desired, edges can intersect without any special or added edge treatment (e.g., radii or chamfers) to facilitation fabrication by cutting or stamping from a sheet of material such as sheet metal.

FIG. 9 is a front view of the hanger 170 of FIG. 7. As described above, the one or more apertures 178 can define the diameter 978. The hook 730 can extend a distance 970 from the middle portion 750 of the elongated body 710 to facilitate engagement of the second end 676 of the hanger 170 with the object 80 (shown in FIG. 6).

Figure 12:
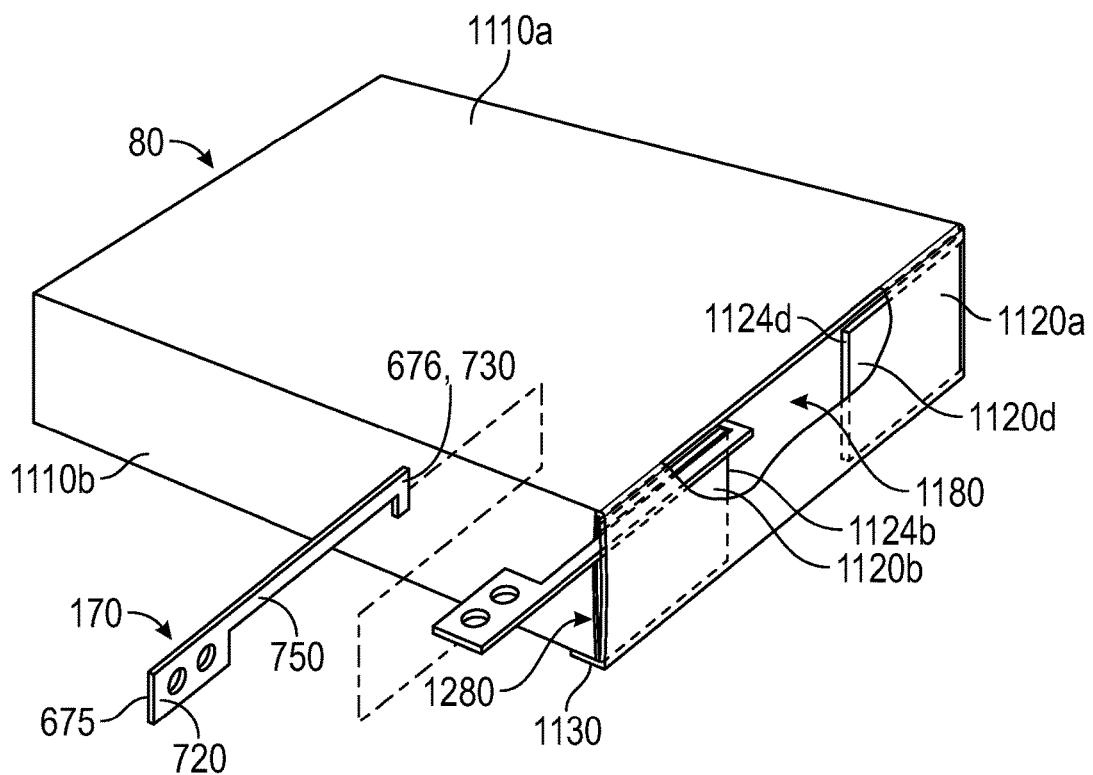
FIG. 12 is a perspective view of the box of FIG. 11 at least partially forming one of the objects 80 of FIG. 1 after full assembly showing the hanger of FIG. 7 in accordance with another aspect of the current disclosure received and captured therein.

FIG. 10 is a front view of the hanger 170 of FIG. 7 in accordance with another aspect of the current disclosure. In some aspects, as shown, the apertures 178 can extend to an edge of the first portion 720 of the elongated body 710. More specifically, a slot or opening 1078, which can be a considered a portion of the corresponding aperture 178, can extend from an edge of the first portion 720 to a remaining portion of any or all of the one or more apertures 178. The hook 730, which can define a "J" shape as shown, can define the aforementioned distance 970, which can be an internal gap. In some aspects, the gap 970 can be constant along the longitudinal direction 913 of the elongated body 710. In some aspects, the gap 970 can be vary along the longitudinal direction 913 of the elongated body 710 to facilitate use with box panel materials of varying thicknesses and/or to ease engagement of the hook 730 with the panel by making an entrance of the gap 970 larger. The gap 970 can be sized to receive and engage a portion of the object 80 suspended from the hanger 170 during use. As shown in FIG. 12, an overall length 1010 of the elongated body 710 and a clear length 1012 defined between the first portion 720 and the hook 730 of the elongated body can be sufficiently long to facilitate engagement between the hook 730 and the object 80. In some aspects, the lengths and proportions of the noted dimensions and any others, as well as the number and location of the apertures 178, can vary to accommodate particular types of objects 80 or the systems 100 in which they are processed.

Figure 11:
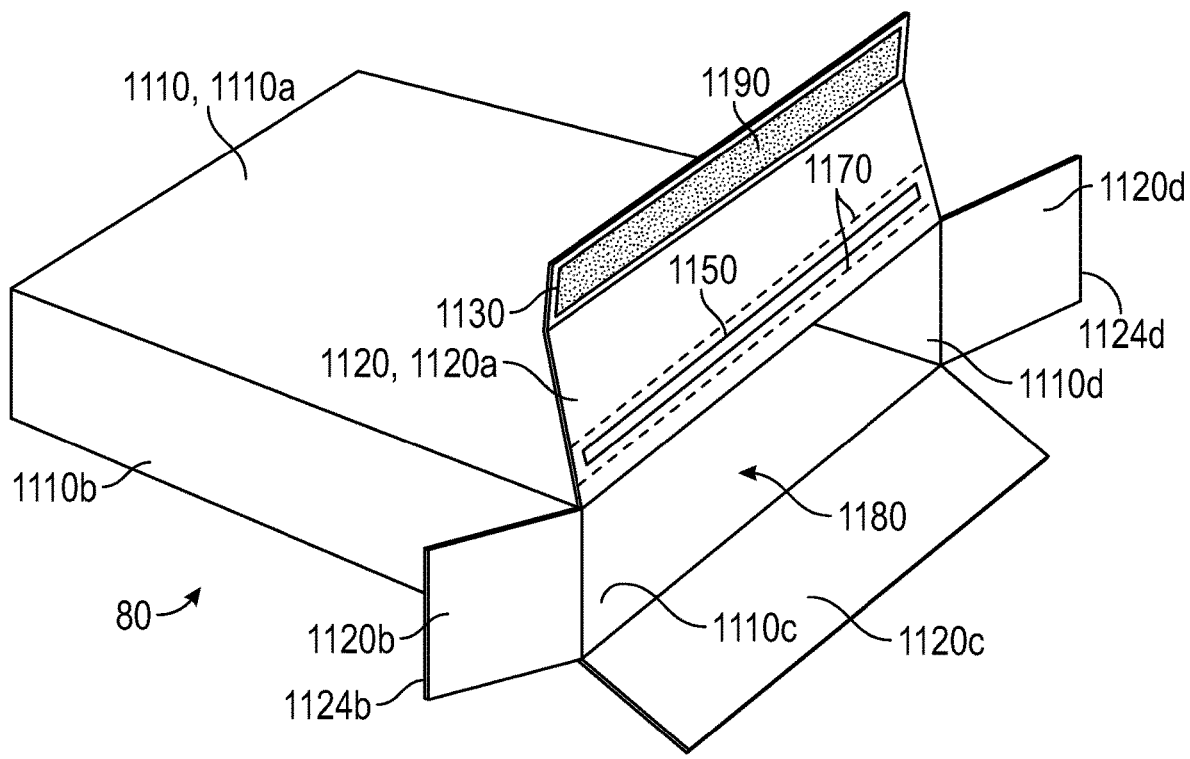
FIG. 11 is a perspective view of a partially assembled box at least partially forming one of the objects of FIG. 1 in accordance with one aspect of the current disclosure.

FIG. 11 is a perspective view of a partially assembled box at least partially forming one of the objects 80 of FIG. 1 in accordance with one aspect of the current disclosure. The box can comprise one or more side walls or side panels 1110, one or more end panels or a first end cap 1120, and a second end cap (not shown). More specifically, the one or more side panels 1110 can comprise a first side panel 1110a, a second side panel 1110b, a third side panel 1110c, and a fourth side panel 1110d. The first side panel 1110a can be positioned adjacent to and can be joined to the fourth side panel 1110d. The second side panel 1110b can be positioned adjacent to and can be joined to the first side panel 1110a. The third side panel 1110c can be positioned adjacent to and can be joined to the second side panel 1110b. The fourth side panel 1110d can be positioned adjacent to and can be joined to the third side panel 1110c. The one or more side panels 1110 and, more specifically, the one or more side panels 1110a,b,c,d can together at least partially define an internal cavity 1180 of the box.

More specifically, the one or more end panels 1120a,b,c,d can comprise a first end panel 1120a, a second end panel 1210b, a third end panel 1120c, and a fourth end panel 1120d. The first end panel 1120a can be positioned adjacent to each of the fourth end panel 1120d and the first side panel 1110a and can be joined to the first side panel 1110a. The second end panel 1120b can be positioned adjacent to each of the first end panel 1120a and the second side panel 1110b and can be joined to the second side panel 1110b. The third end panel 1120c can be positioned adjacent to each of the second end panel 1120b and the third side panel 1110c and can be joined to the third side panel 1110c. The fourth end panel 1120d can be positioned adjacent to each of the third end panel 1120c and the third side panel 1110c and can be joined to the third side panel 1110c. The first end cap 1120 and the aforementioned second end cap and, more specifically, the one or more end panels 1120a,b,c,d can likewise together at least partially define an internal cavity 1180 of the box.

Any portion of an end cap such as the end cap 1120 can define various edges that can be engaged by the hook 730 (shown in FIG. 12) of the hanger 170 (shown in FIG. 12). More specifically, as shown, the second end panel 1120b can define an edge 1124b, which can be substantially parallel to a joint between the second end panel 1120b and the second side panel 1110b. Similarly, the fourth end panel 1120d can define an edge 1124d, which can be substantially parallel to a joint between the fourth end panel 1120d and the fourth side panel 1110d.

Any portion of an end cap such as the first end cap 1120 can comprise additional panels to facilitate closure of the box—with or without a separate fastener such as tape. More specifically, in some aspects, a flap panel 1130 can extend from an end panel such as, for example and without limitation, the first end panel 1120a and can, as shown in FIG. 12 secure the first end panel 1120a to the third side panel 1110c upon closure of the box. The flap panel 1130 can comprise a fastener 1190, which can comprise a layer or strip of adhesive, with or without a release liner that can be removed immediately before closure of the box.

Any of the one or more side panels 1110 or an end cap such as the first end cap 1120 can comprise additional features, as will be described below, to facilitate a method of sterilizing the object 80 by hanging the object 80 while bathed in UV light. More specifically, in some aspects, a reinforcement strip 1150 can be affixed or integrated into a side panel or an end panel such as, for example and without limitation, the first end panel 1120a. On one or both sides of the reinforcement strip 1150, the box can define perforated tear cuts or tear lines 1170, which can facilitate later opening of the box and/or hanging of the box when, as will be described below, the hanger 170 is integral to and/or formed in the object itself. When pulling a strip of material, which can be tear strip, of the first end panel 1120a, for example, the reinforcement strip 1150 can prevent premature tearing of the strip of material by adding strength to the strip of material, while the perforated tear lines 1170 can facilitate predictable and clean removal of the strip of material from the box.

FIG. 12 is a perspective view of the box of FIG. 11 at least partially forming one of the objects 80 of FIG. 1 after full assembly showing the hanger 170 of FIG. 7 in accordance with another aspect of the current disclosure received and captured therein. As shown, the second end 676 of the elongated body 710 and, more generally, the hanger 170 can be inserted into an opening in the object 80 such as the opening 1280 and can be partially rotated to engage the hook 730 of the hanger 170 with the object 80. More specifically, the hook 730 of the hanger 170 can engage an internal edge of the box such as, for example and without limitation, the edge 1124b of the second end panel 1120b. The first end 675 of the elongated body 710 can remain protruding out of the object 80, and can be connected or fastened to the external hanger-receiving retainer 120 (shown in FIG. 1) or, more specifically, a retaining hook 122 (shown in FIG. 1) thereof to suspend the object 80 from the hanger-receiving retainer 120. The object 80 can comprise any type of package or parcel such as, for example and without limitation, an envelope, a box, a tube, or a bag.

Minimizing each of the thickness 810 (shown in FIG. 8) and the width 817 (shown in FIG. 8) of the elongated body 710 of the hanger 170 can facilitate insertion and rotation of the hanger 170 into the opening 1280 and help avoid unnecessary distortion of the object 80. In some aspects, the hanger 170 can be inserted into an opening on an opposite side of the box—for example and without limitation, into a space defined between the first end panel 1120a and the fourth end panel 1120d—or into an opening defined in the second end cap on an opposite end of the box. When otherwise sealed with tape or another sealing device, the hook can cut or punch through same before engaging with an internal panel of the box as described herein.

FIGS. 13-20 show various aspects of the object 80 comprising or defining an integral hanger 170, i.e., a hanger that is formed integrally with or embedded in the object 80. FIG. 13 is a top perspective view of the object 80 of FIG. 1 in accordance with another aspect of the current disclosure. As shown, the object 80 can comprise a shipping tube and an integrated hanger 170 in a non-extended position. The hanger 170 can be integrated into the object 80 to form a device comprising the object 80 and a hanger 170, which can be positioned on or embedded into an outer surface of the object 80. More specifically, the elongated body 710 of the hanger 170 can be releasably connected to or embedded in the outer surface of the object 80. Again, the hanger 170 can comprise the first end 675 and the second end 676. The hanger 170 can comprise a fastener at the first portion 720, which can comprise or define a loop or aperture as shown and can be secured to the middle portion 750 of the elongated body 710. Again, the middle portion 750 can extend between the first end 675 and the second end 676. In some aspects, the second end 676 of the hanger 170 can be integrally connected or secured—even permanently—to the object 80 with a fastener or by otherwise engaging the second end 676 through a hole or other portion of the end cap 1120 of the object 80. The UV indicator 770 (shown in FIG. 14) can be hidden under a cover 1370, which can be opaque and can prevent premature exposure of the UV indicator 770 to UV light by blocking UV light from reaching the UV indicator. The cover 1370 can be a label, a bag, a film, or any other structure that shields the UV indicator 770 from UV light until a user of the system 100 is ready to use the hanger 170 and "activate" the UV indicator 770.

FIG. 14 is a top perspective view of the object 80 of FIG. 13 with the integrated hanger 170 in an extended position. As shown, release of the hanger 170 into the extended position can release the cover 1370—or the cover 1370 can be released or removed manually—and thereby expose the UV indicator 770. A dashed line surrounding the UV indicator 770 shows the previous position of the cover 1370.

Figure 15:
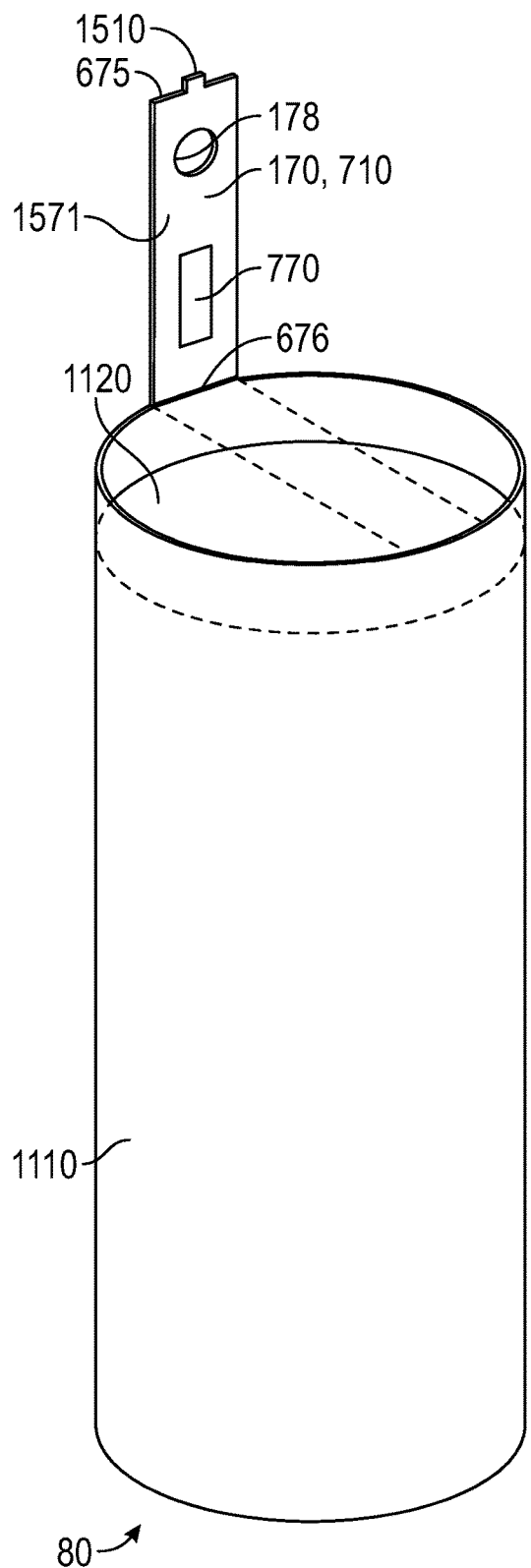
FIG. 15 is a top perspective view of the object of FIG. 13 with the integrated hanger in an extended position and in accordance with another aspect of the current disclosure.

FIG. 15 is a top perspective view of the object 80 of FIG. 13 with the integrated hanger 170 in an extended position and in accordance with another aspect of the current disclosure. As shown, the hanger 170 can be formed monolithically with the end cap 1120. More specifically, a portion of the end cap 1120 comprising the hanger 170 or the entire end cap 1120 can be monolithic, i.e., it can be formed as a singular component that constitutes a single material without joints or seams and can remain so formed. In other aspects, the hanger 170 can be formed separately from the end cap 1120 and joined to the end cap 1120 with a fastener. In some aspects, as shown, a plastic hinge can be incorporated or defined into the hanger 170 at a connection between the second end 676 of the hanger 170 and the end cap 1120. As shown, the UV indicator 770 can be fixed to an underside or lower surface 1571 of the hanger 170, which can bent down to face the remaining portion of the end cap 1120, as shown by a position represented by the parallel broken construction lines extending across a diameter of the end cap 1120.

Figure 16:
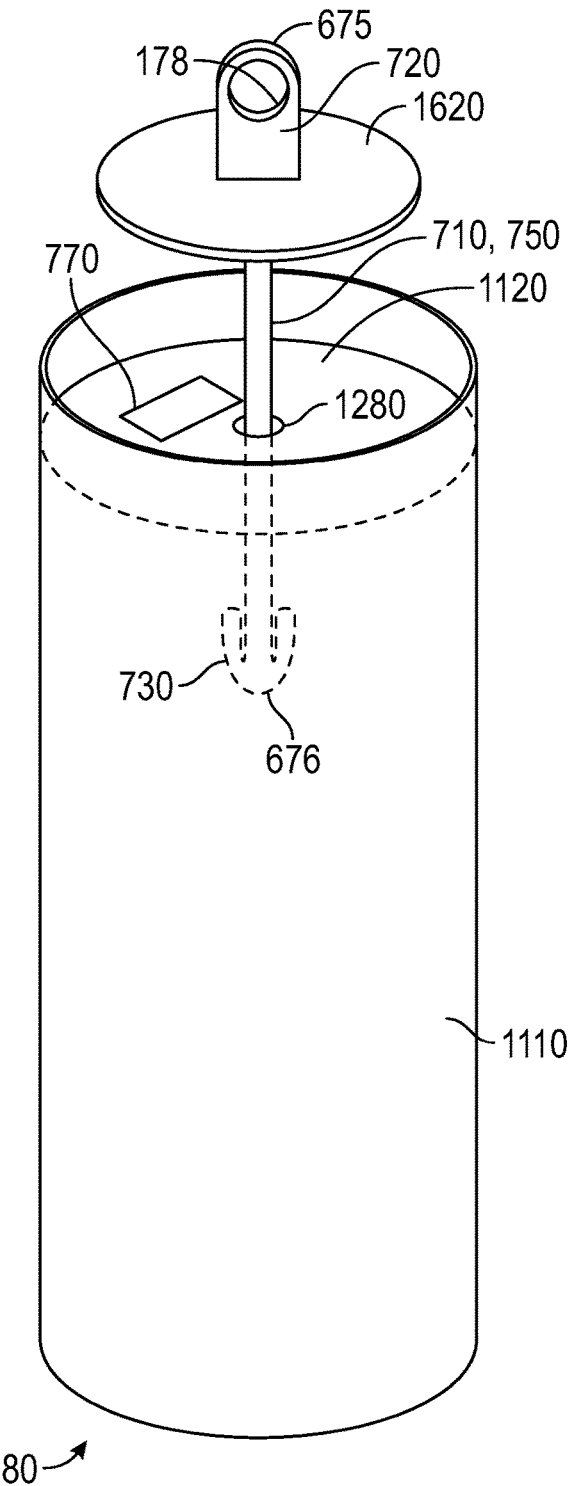
FIG. 16 is a top perspective view of the object of FIG. 13 with the integrated hanger in a partially extended position and in accordance with another aspect of the current disclosure.

FIG. 16 is a top perspective view of the object 80 of FIG. 13 with the integrated hanger 170 in a partially extended position and in accordance with another aspect of the current disclosure. The first portion 720 of the hanger 170 can comprise a flange 1620, which can cover the UV indicator strip 770 when the hanger 170 is in the non-extended position. The second end 676 of the hanger 170 can extend through the opening 1280, which can be defined in the end cap 1120, and the hook 730, which can comprise a double barb as shown, at the second end 676 of the hanger 170 can engage with the opening 1280 to secure the hanger 170 to the object 80.

Figure 17:
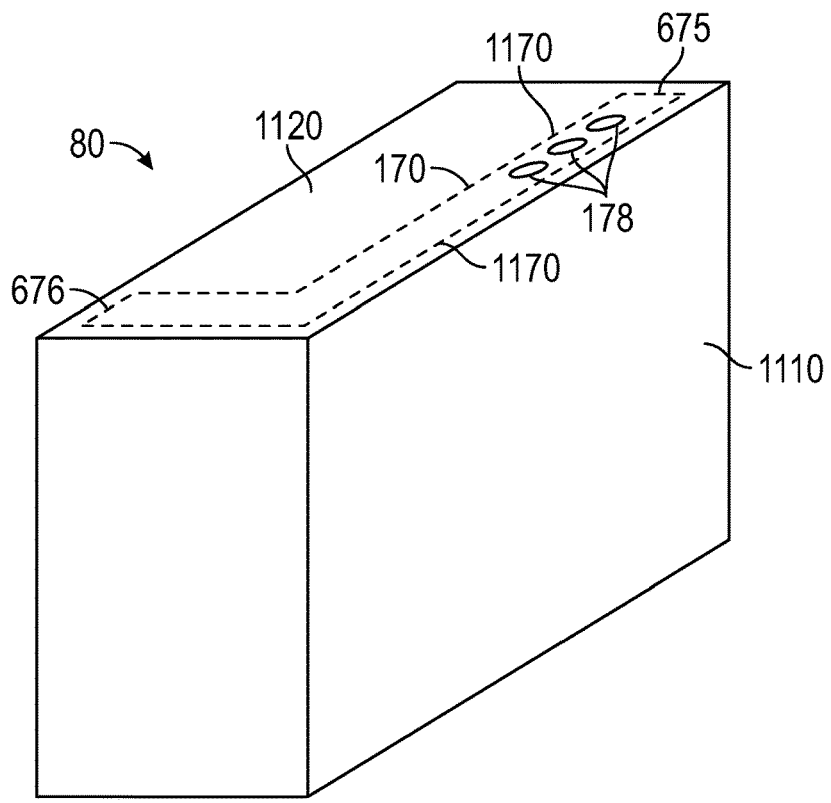
FIG. 17 is a perspective view of the object of FIG. 1 as a box defining an integrated hanger and in accordance with another aspect of the current disclosure.
Figure 18:
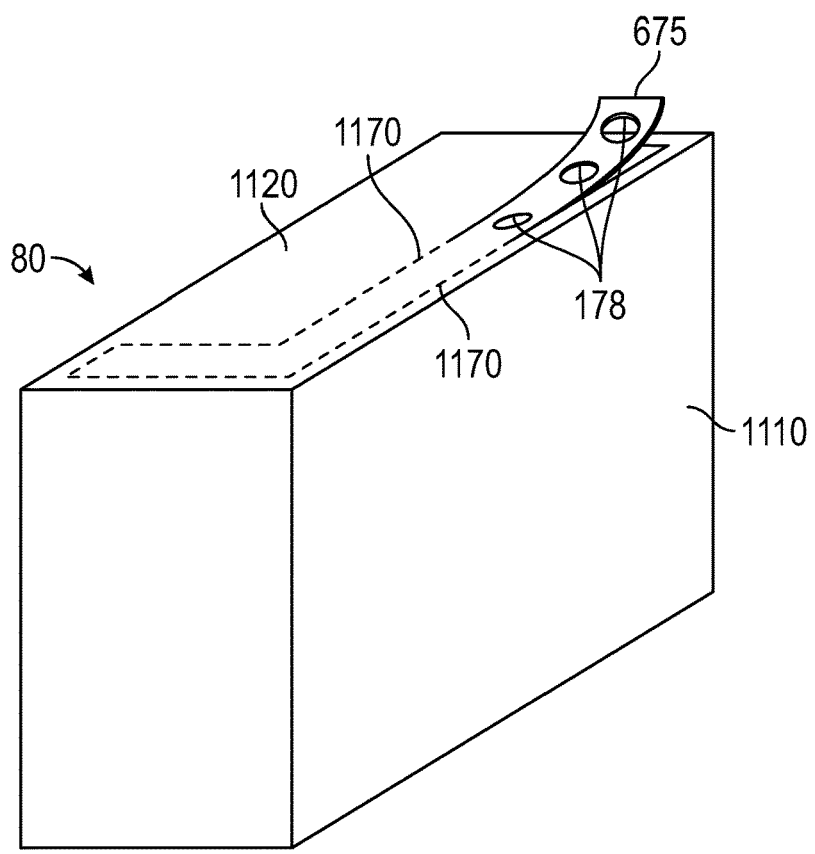
FIG. 18 is a perspective view of the object of FIG. 17 with the integrated hanger partially released or separated from the box.
Figure 19:
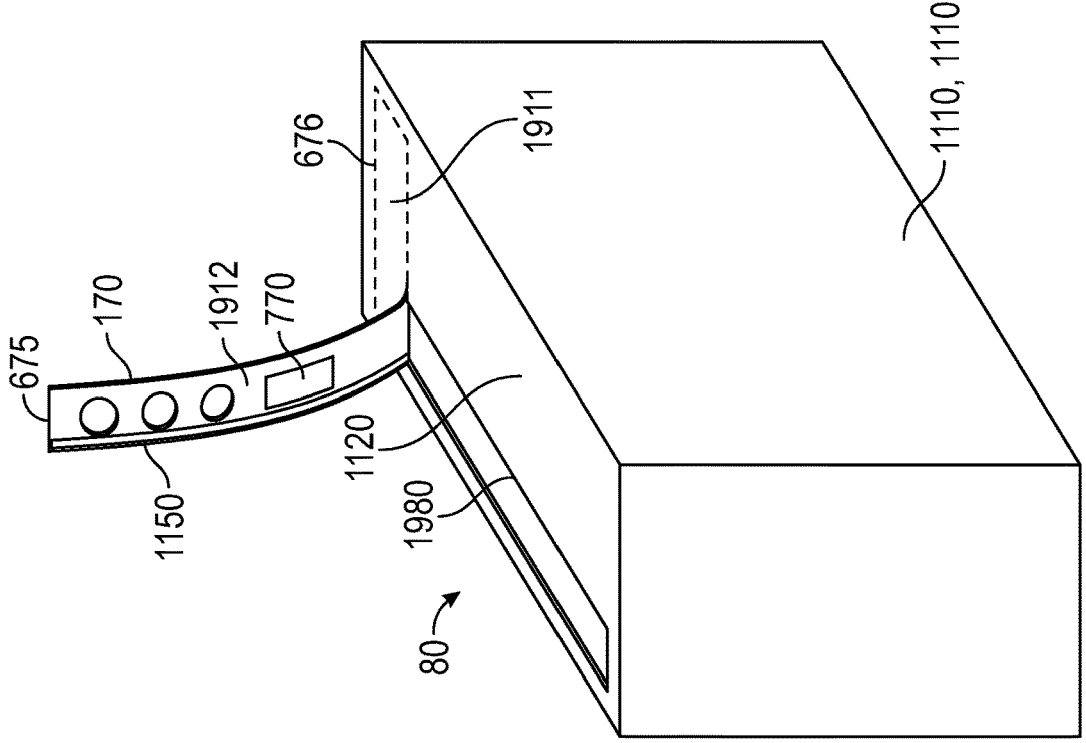
FIG. 19 is a perspective view of the object of FIG. 17 with the integrated hanger partially released from the box and exposing a UV indicator.

FIGS. 17-19 show the object 80 of FIG. 1 as a box defining an integrated hanger 170 and in accordance with another aspect of the current disclosure. In some aspects, the box can be made from any one of a variety of paper-based materials such as, for example and without limitation, cardboard or paperboard. In some aspects, the box can be made from any one of a variety of non-paper-based materials. FIG. 17 is a perspective view of the object 80 before the first end 675 or any other portion of the hanger 170 is manipulated and showing the hanger 170 defined by the perforated tear lines 1170. As shown, the hanger 170 can be integrated into a tab used to open the object 80. The perforated tear lines 1170 can extend across any side panel or end panel of the object 80. In some aspects, the perforated tear lines 1170 can extend the full length drawn. In other aspects, the perforated tear lines 1170 can extend only partially across the box. In any case, the hanger 170 can be configured to partially release from the object 80 but not fully release and separate from the object 80, if at all, until such time as a user may so desire and either cut or pull the hanger 170 from the object 80 with sufficient force. FIG. 18 is a perspective view of the object 80 of FIG. 17 with the hanger 170 partially released from the box. As shown in FIG. 18, the first end 675 and the elongated body 610 of the hanger 170 can be disconnected or separated from the object 80 by pulling the first end 675. Once separated from the object 80, the first end 675, which can define the apertures 178, can be connected to the hanger-receiving retainer 120 of the system 100 as described above, and the object can then be irradiated with UV radiation from the system 100.

More specifically, the first end 675 of the elongated body 710 can be at least partially releasable from a surrounding panel or surface of the object 80, and the second end 676 of the elongated body 710 can be sufficiently secured to the surrounding surface of the object 80 to support the weight of the object 80 and the contents for which the object 80 (e.g., the box shown) is configured for use.

FIG. 19 is a perspective view of the object 80 of FIG. 17 with the integrated hanger 170 partially released from the box and exposing the UV indicator 770. The elongated body 710 of the hanger 170 can define an outer surface 1911 defining also an outer surface of the object 80, and the elongated body can define an inner surface 1912 opposite or distal from the outer surface 1911. The UV indicator 770 can be positioned on or defined in the inner surface 1912. In some aspects, as shown, the UV indicator 770 can be positioned on a surface of the hanger 170 that is facing the object 80, i.e., facing inward, when the hanger 170 is positioned on or embedded into the outer surface of the object 80. The UV indicator 770 can be thereby exposed when the first end 675 and optionally the elongated body 710 are disconnected or separated from the object 80. In some aspects, the UV indicator 770 can be present on the outer surface of the object 80 and can be covered by the first end 575 and/or the elongated body 710 of the hanger 170 when the hanger 170 is positioned on or embedded into the outer surface of the object 80. In some aspects, as shown in both FIGS. 19 and 20, portions of the hanger 170 such as the second end 676 and the elongated body 710 can be components of a tape positioned on the outer surface of the object 80. While not shown, such tape can be shaped similarly as any one or more portions of the hanger 170 and can be reinforced with the reinforcement strip 1150.

Upon separation of the first end 675 and optionally other portions of the hanger 170 from surrounding portions of the object 80, an opening 1980 can be defined in a surface of the object 80. Behind the opening 1980, one or more panels formed by side panels or end panels of the box forming the object 80, or a plastic or paper film or other barrier can block access to the contents of the box or other object 80 when such contents might otherwise be exposed.

Figure 20:
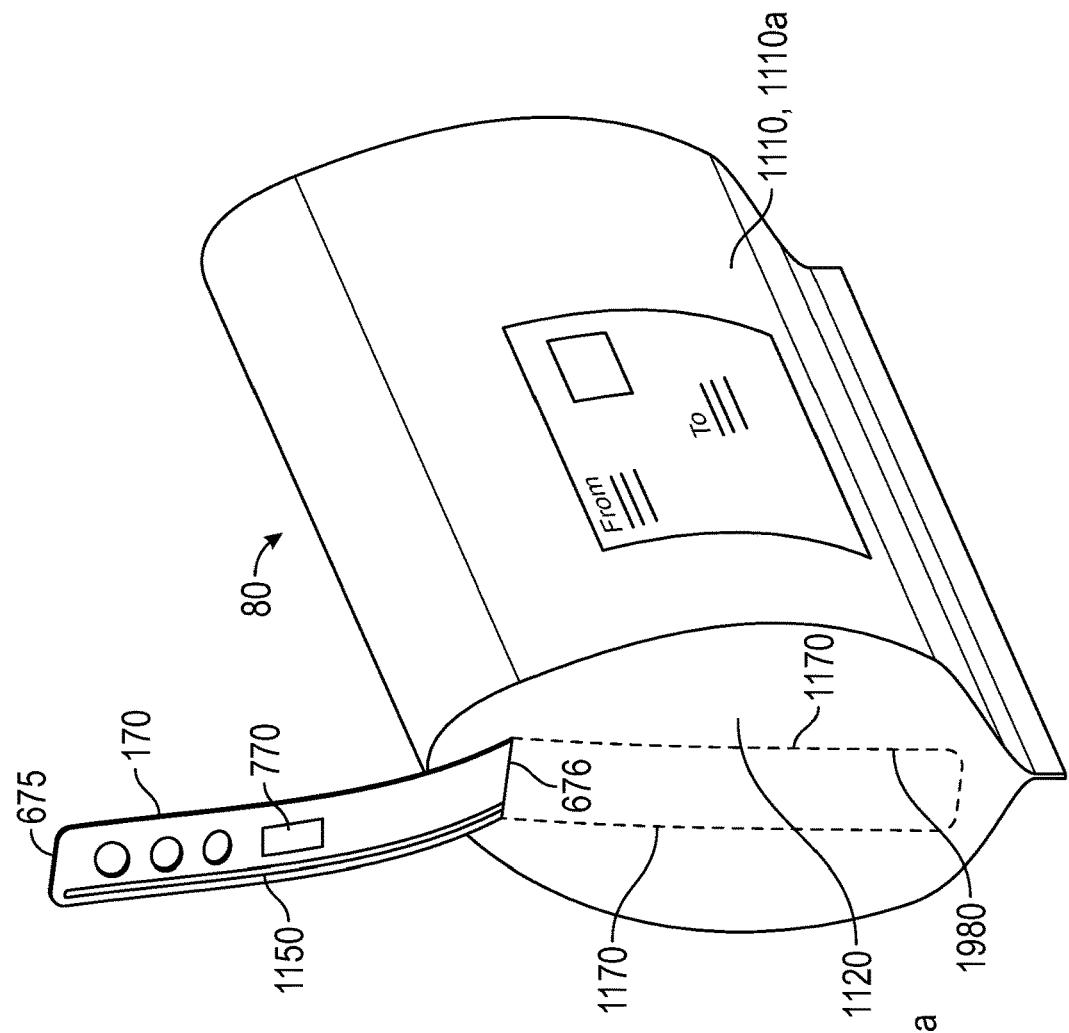
FIG. 20 is a perspective view of the object of FIG. 1 as a flexible package defining the integrated hanger and in accordance with another aspect of the current disclosure, the integrated hanger shown partially released from the flexible package and exposing the UV indicator.

FIG. 20 is a perspective view of the object 80 of FIG. 1 as a flexible package defining the integrated hanger 170 and in accordance with another aspect of the current disclosure, the integrated hanger 170 shown partially released from the flexible package and exposing the UV indicator 770. While the hanger 170 and accompanying features are shown integrally formed in the end cap 1120, the hanger 170 can be integrally formed in any surface of an object and in any one of a variety of orientations.

A method of using the system 100 and, more specifically, irradiating the object 80 can comprise inserting the second end 676 of the hanger 170 into the opening 1280 in the object 80. The method can comprise suspending the object 80 from the second end 676 of the hanger 170. The method can comprise irradiating the object 80 with UV radiation from the UV generator 110. The method can comprise inserting the hanger 170 in and suspending the object 80 from a portion of the enclosure 230 prior to the UV radiation exposure. More specifically, the method can comprise attaching the first end 675 of the hanger 170 to the hanger-receiving retainer 120, which can be positioned in the enclosure 230. In some aspects, the method can comprise rotating and/or translating the hanger 70 and the object 80 within the enclosure 230. In some aspects, the method can comprise removing the cover 1370 from the elongated body 710 of the hanger 170 or from the object 80 to expose the UV indicator 770 prior to irradiating the object 80.

In some aspects, a method of using the discrete hanger 170 can comprise inserting the second end 676 of the hanger 170 into a hanger-receiving opening 1280 defined in the object 80. The thickness 810 of the elongated body 710 and the width 817 of the portion of the elongated body 710 being, in each of a transverse direction 714 of the elongated body 710 and a direction normal to the transverse direction 714, can be sized to be received within the hanger-receiving opening 1280 defined in the object. The method can comprise suspending the object 80 from the second end of the hanger 170. The method can comprise irradiating the object 80 with UV radiation from the UV generator 110. More specifically, inserting the second end of the hanger into the hanger-receiving opening defined in the object comprises inserting the second end of the hanger into a space defined between two panels of a closed box defining the object and rotating the hanger to engage the hook with one of the two panels.

In some aspects, a method of using the integral hanger 170 can comprise separating the first end 675 of the hanger 170 from the object 80. The method can comprise the second end 676 of the hanger 170 remaining secured to the object 80. The method can comprise suspending the object 80 from the second end 676 of the hanger 170. The method can comprise irradiating the object 80 with UV radiation from the UV generator 110.

In some aspects, the method can comprise exposing the UV indicator 770 to the UV radiation from the UV generator 110, where the UV indicator can be adhered to one of the object 80 and the hanger 170.

One should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily comprise logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which comprise one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A hanger comprising:
   an elongated body defining:
   a first end defining at least one aperture; and
   a second end comprising a hook, the hook defining one of a "J" shape, an "L" shape, and a barb shape, the first end and the second end defined at opposite ends of the hanger along a longitudinal direction, a width of a portion of the elongated body between the first end and the second end being narrower than each of a width of the elongated body at the first end and a width of the elongated body at the second end, the hanger being configured to support a hanging object at the second end; and
   a UV indicator.

2. The hanger of claim 1, wherein the UV indicator is configured to change appearance upon exposure to UV light.

3. The hanger of claim 2, wherein the UV indicator is adhered to a surface of the elongated body.

4. The hanger of claim 3, wherein the UV indicator comprises one of paint and ink.

5. The hanger of claim 3, wherein a cover is positioned over the UV indicator, the cover configured to selectively block UV light from reaching the UV indicator.

6. The hanger of claim 1, wherein the first end defines a plurality of apertures extending in the longitudinal direction of the elongated body.

7. A system comprising:
   the hanger of claim 1;
   a UV generator configured to irradiate an object suspended from the hanger with UV light; and
   a hanger-receiving retainer configured to receive the hanger.

8. The system of claim 7, further comprising an enclosure; each of the hanger, the UV generator, and the hanger-receiving retainer being positioned inside the enclosure during operation of the system.

9. The system of claim 8, wherein the hanger-receiving retainer is dynamically mounted.

10. A method comprising:
    suspending an object with the hanger of claim 1; and
    irradiating the object with UV radiation from a UV generator configured to activate the UV indicator.

11. The method of claim 10, wherein suspending the object with the hanger comprises translating and/or rotating the object.

12. The method of claim 10, wherein irradiating the object with UV radiation comprises changing a color defined by the UV indicator.

13. A method of using the hanger of claim 1, comprising:
    inserting the second end of the hanger into a hanger-receiving opening defined in the object, the width of the portion of the elongated body being, in each of a transverse direction of the elongated body and a direction normal to the transverse direction, sized to be received within the hanger-receiving opening defined in the object;
    suspending the object from the second end of the hanger; and
    irradiating the object with UV radiation from a UV generator.

14. The method of claim 13, wherein inserting the second end of the hanger into the hanger-receiving opening defined in the object comprises inserting the second end of the hanger into a space defined between two panels of a closed box defining the object and rotating the hanger to engage the hook with one of the two panels.

15. A method comprising:
    obtaining a hanger comprising:
        an elongated body defining:
            a first end defining at least one aperture; and
            a second end, the first end and the second end defined at opposite ends of the hanger along a longitudinal direction, a width of a portion of the elongated body between the first end and the second end being narrower than each of a width of the elongated body at the first end and a width of the elongated body at the second end, the hanger being configured to support a hanging object at the second end; and
        a UV indicator;
    inserting the second end of the hanger into a hanger-receiving opening defined in the object, the width of the portion of the elongated body being, in each of a transverse direction of the elongated body and a direction normal to the transverse direction, sized to be received within the hanger-receiving opening defined in the object;
    suspending the object from the second end of the hanger; and
    irradiating the object with UV radiation from a UV generator.

16. The method of claim 15, wherein inserting the second end of the hanger into the hanger-receiving opening defined in the object comprises inserting the second end of the hanger into a space defined by the object and engaging the object with the second end.

17. The method of claim 15, wherein the UV indicator is adhered to a surface of the elongated body.

18. The method of claim 15, wherein the UV indicator comprises one of paint and ink.

19. A hanger comprising:
    an elongated body defining:
        a first end defining at least one aperture; and
        a second end comprising a hook, the first end and the second end defined at opposite ends of the hanger along a longitudinal direction, the hanger being configured to support a hanging object at the second end; and
    a UV indicator.

20. The hanger of claim 19, wherein the UV indicator is adhered to a surface of the elongated body.

\* \* \* \* \*